United States Patent
Carling et al.

(10) Patent No.: US 6,448,249 B1
(45) Date of Patent: ***Sep. 10, 2002

(54) SUBSTITUTED 1,2,4-TRIAZOLO[3,4-A] PHTHALAZINE DERIVATIVES AS GABAα5 LIGANDS

(75) Inventors: William Robert Carling, Bishops Stortford; Tamara Ladduwahetty, London; Angus Murray MacLeod, Bishops Stortford; Kevin John Merchant, Stevenage; Kevin William Moore, Buntingford; Francine Sternfeld, London; Leslie Joseph Street, Little Hallingbury, all of (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/600,988

(22) PCT Filed: Feb. 17, 1999

(86) PCT No.: PCT/GB99/00485

§ 371 (c)(1),
(2), (4) Date: Jul. 24, 2000

(87) PCT Pub. No.: WO99/43677

PCT Pub. Date: Sep. 2, 1999

(30) Foreign Application Priority Data

Feb. 25, 1998 (GB) ............................................. 9803992
May 6, 1998 (GB) ............................... PCT/GB98/01307
Nov. 12, 1998 (GB) ............................................. 9824896

(51) Int. Cl.⁷ ................... A61K 31/5025; C07D 487/04
(52) U.S. Cl. ....................................... 514/248; 544/234
(58) Field of Search ........................... 514/248; 544/234

(56) References Cited

U.S. PATENT DOCUMENTS

| 4,788,186 A | 11/1988 | Occelli et al. |
| 5,145,684 A | 9/1992 | Liversidge et al. |
| 6,200,975 B1 * | 3/2001 | Carling et al. ............... 514/248 |

FOREIGN PATENT DOCUMENTS

| EP | 0 085 840 | 8/1983 |
| EP | 0 134 946 | 3/1985 |
| WO | WO96/25948 | 8/1996 |
| WO | WO98/04560 | 2/1998 |
| WO | WO98/50385 | 11/1998 |

OTHER PUBLICATIONS

Cai, D., et al., Tetrahedron Lett., 15:2537–2540 (1996).
Holzer, W., et al., J. Heterocyclic. Chem., 29:1203–1207 (1992).
McNamara, R.K., et al., Psychobiology, 21:101–108 (1993).
Tarzia, et al., I1 Farmaco—Ed. Sc., 43:189–201 (1987).

* cited by examiner

*Primary Examiner*—Patricia L. Morris
(74) *Attorney, Agent, or Firm*—J. Eric Thies; Shu Muk Lee; Melvin Winoker

(57) ABSTRACT

A substituted triazolopyridazine derivative, its use in cognition enhancement therapy, compositions containing it and processes for its manufacture.

2 Claims, No Drawings

SUBSTITUTED 1,2,4-TRIAZOLO[3,4-A] PHTHALAZINE DERIVATIVES AS GABAα5 LIGANDS

This is an application under 35 U.S.C. 371 of PCT/GB99/00485 and claims priority from Great Britain Application No. 9803992.8 filed Feb. 25, 1998, Great Britain Application No. 9824896.6 filed Nov. 12, 1998, and International Application No. PCT/GB98/01307 filed May 6, 1998.

The present invention relates to a substituted triazolopyridazine derivative, to its use in therapy, to compositions containing it and to a process for its manufacture.

We have now discovered that it is possible to obtain medicaments which have cognition enhancing effects which may be employed with less risk of proconvulsant effects previously described with benzodiazepine receptor partial or full inverse agonists. Inverse agonists which are inverse agonists for the α5 receptor and are relatively free of activity at α1, α2, and α3 receptor binding sites are preferred.

European Patent Applications 0085840 and 0134946 describe related series of 1,2,4-triazolo[3,4-a]phthalazine derivatives which are stated to possess antianxiety activity. However, there is no disclosure nor any suggestion in either of these publications of the compounds of the present invention, nor that the compounds disclosed in the Applications have any cognition enhancing properties.

The present invention provides a compound which is:
3-(5-methylisoxazol-3-yl)-6-(1-methyl-1,2,3-triazol-4-yl)methyloxy-1,2,4-triazolo[3,4-a]phthalazine.

Cognition enhancement can be shown by testing the compound in the Morris watermaze as reported by McNamara and Skelton, Psychobiology, 21:101–108. The functional efficacy at the various receptor subtypes can be calculated using the method disclosed in WO-A-9625948.

Thus, for example, the compound of the present invention can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS.

The invention also provides pharmaceutical compositions comprising the compound of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycel, and other pharmaceutical diluents, e.g. water, to form a solid preformulation composition containing a homogeneous mixture of the compound of the present invention, or a pharmaceutically acceptable salt thereof. When referring to these preformulation compositions a homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The present invention further provides the use of the compound of the present invention in the manufacture of a medicament for the enhancement of cognition, preferably in a human suffering from dementing illness such as Alzheimer's disease.

For the enhancement of cognition, a suitable dosage level is about 0.01 to 250 mg/kg per day, preferably about 0.01 to 100 mg/kg per day, and especially about 0.01 to 5 mg/kg of body weight per day. The compound may be administered on a regimen of 1 to 4 times per day. In some cases, however, dosage outside these limits may be used.

It is preferred that the compound of the present invention be ground, for example using a pestle and mortar or industrial equivalent thereto, to a particle size of between 1 and 10 $\mu$M, and preferably less than 5 $\mu$M, before formulation. The compound may be micronised or sonicised by methods known in the art or nanonised, for example by methods disclosed in U.S. Pat. No. 5,145,684.

The present invention also provides a process for the production of the compound of the present invention, which comprises reacting a methylating reagent, such as lithium hexamethyldisilazide with 3-(5-methylisoxazol-3-yl)-6-(1H-1,2,3-triazol-5-yl)methyloxy-1,2,4-triazolo[3,4-a]phthalazine.

The reaction is generally carried out in a solvent such as DMF, generally at a temperature below 0° C. with warming to about room temperature and generally under an inert gas such as nitrogen. The reaction mixture is generally allowed to stand for 4–12 hours. The desired product is generally purified from other reaction products by a conventional separation technique such as preparative HPLC.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons 1991. The protecting groups may be removed at a convenient subsequent stage using methods known from the art.

The compound in accordance with this invention potently inhibit the binding of [$^3$H]-flumazenil to the benzodiazepine binding site of human $GABA_A$ receptors containing the α5 subunit stably expressed in Ltk$^-$ cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 10 nM; for α5β3γ2: 1.0nM).

50 μl of buffer or solvent carrier (e.g. 10% DMSO) if compound is dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filter followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for the test compound.

The compound in accordance with this invention potently inhibits the binding of [$^3$H]-flumazenil to the benzodiazepine minding site of human $GABA_A$ receptors containing the α5 subunit stably expressed in Ltk$^-$ cells.

The compound of the accompanying Example was tested in the above assay, and was found to possess a $K_i$ value for displacement of [$^3$H]Ro 15-1788 from the α5 subunit of the human $GABA_A$ receptor of 100 nM or less.

The compound of the present invention has been shown to enhance cognition in the rat water maze test (Morris, Learning and Motivation, 1981, 12, 239ff). Further details of methodology for demonstrating that the present compounds enhance cognition can be found in WO-A-9625948. This has been demonstrated at a minimum effective dose of 0.3 mg/kg at which the compound of the present invention has 40% receptor occupancy. It has also been demonstrated at a dose of 3 mg/kg.

The compound of the present invention can be made as described in following Examples. Precise details of the reaction conditions, and obvious modifications of the reaction procedure, are well within the capabilities of the skilled person.

INTERMEDIATE 1

6-Chloro-3-(5-Methylisoxazol-3-yl)-1,2,4-triazolo[3,4-a]phthalazine a) 1-Chloro-4-hydrazinophthalazine 1,4-Dichlorophthalazine (20.0 g, 0.100 mol) was added to a boiling solution of hydrazine monohydrate (37.3 ml, 0.765 mol) in ethanol (500 ml) and the mixture heated at reflux for 0.5 h. The mixture was cooled to room temperature and the solid collected by filtration and washed with ether. The material was taken with n-butanol and ammonia solution (sp. gr. 0.91) and heated until the solid dissolved. The organic layer was separated, evaporated in vacuo and the residue azeotroped with xylene (×2) and dried in vacuo to give the title-hydrazine (11.5 g, 59%), $^1$H NMR (250 MHz, $d^6$-DMSO) δ7.84–8.04 (3H, m, Ar—H), 8.20 (1H, m, Ar—H); MS (ES$^+$) m/e 194 [MH]$^+$.

b) 5-Methylisoxazole-3-carboxylic acid

A mixture of acetonylacetone (10 g, 88 mmol) and nitric acid (sp. gr. 1.42)/water (2:3) (50 ml) was cautiously brought to reflux under a stream of nitrogen and boiled for 1 h. The solution was cooled to room temperature and aged overnight. The resultant solid was collected by filtration, washed with chilled water (2×7 ml) and hexane, and dried in vacuo to give the title-acid (4.4 g, 40%), $^1$H NMR (CDCl$_3$) δ2.50 (3H, d, J=0.8 Hz, Me), 6.41 (1H, d, J=0.8 Hz, Ar—H).

c) 6-Chloro-3-(5-Methylisoxazol-3-yl)-1,2,4-triazolo[3,4-a]phthalazine

5-Methylisoxazole-3-carboxylic acid (5.24 g, 41.3 mmol), bis(2-oxo-3-oxazolidinyl)phosphinic chloride (10.5 g, 41.2 mmol) and triethylamine (11.5 ml, 82.5 mmol) were added successively to a stirred suspension of 1-chloro-4-hydrazinophthalazine (8.00 g, 41.2 mmol) in dichloromethane (1 l) at 0° C. under nitrogen. The mixture was stirred at 0° C. for 2 h and at room temperature overnight. The solvent was evaporated in vacuo, the residue triturated with water and the solid filtered off, washed with hexane and dried in vacuo to give the ketohydrazine (11 g), MS (ES$^+$) m/e 304 [MH]$^+$. A solution of the ketohydrazine (11 g) and triethylamine hydrochloride (2.2 g, 20% w/w) in xylene (500 ml) was heated at reflux for 3 h. The mixture was cooled to room temperature and the solvent evaporated in vacuo. The residue was dissolved in dichloromethane, washed with water (×2), dries (MgSO$_4$) and evaporated in vacuo, and the solid recrystallized (dichloromethane/hexane) to give the title-compound (6.8 g, 58%), $^1$H NMR (360 MHz, CDCl$_3$) δ2.59 (3H, s, Me), 6.90 (1H, s, Ar—H), 7.95 (1H, m, Ar—H), 8.07 (1H, m, Ar—H), 8.34 (1H, m, Ar—H), 8.78(1H, s, Ar—H); MS (ES$^+$) m/e 286 [MH]$^+$.

Reference Example 1

3-(5-Methylisoxazol-3-yl)-6-(2-pyridyl)methyloxy1, 2,4-triazolo[3,4-a]phthalazine Sodium hydride (244 mg of a 60% dispersion in oil, 6.10 mmol) was added to a stirred solution of 2-pyridylcarbinol (470 mg, 4.27 mmol) in DMF (60 ml) at room temperature under nitrogen and the mixture stirred for 0.25 h. After this time, Intermediate 1 (1160 mg, 4.07 mmol) was added and the mixture stirred for 2 h. The solvent was removed in vacuo and the residue dissolved in dichloromethane, washed with water (×2), dried (MgSO$_4$) and evaporated in vacuo. Flash chromatography on silica gel eluting with 3% methanol/dichloromethane followed by recrystallisation (dichloromethane/hexane) gave the title-product (640 mg, 44%), mp 234–236° C.; $^1$H NMR (360 MHz, CDCl$_3$) δ2.59 (3H, d, J=0.8 Hz, Me), 5.77 (2H, s, CH$_2$), 6.82 (1H, d, J=0.8 Hz, Ar—H), 7.30 (1H, m, Ar—H), 7.74–7.85 (3H, m, Ar—H), 7.95 (1H, m, Ar—H), 8.33 (1H, d, J=7.8 Hz, Ar—H), 8.64–8.7 (2H, m, Ar—H); MS (ES$^+$) m/e 359 [MH]$^+$; Anal. Found. C, 62.93; H, 3.56; N, 22.94. C$_{19}$H$_{14}$N$_6$O$_2$ 0.05 (CH$_2$Cl$_{12}$) requires C, 63.10; H, 3.92; N, 23.17%.

Reference Example 2

6-(6-Bromopyridin-2-yl)methyloxy-3-(5-methylisoxazol-3-yl)-1,2,4-triazolo[3,4-a]phthalazine The title-compound was prepared from Intermediate 1 and 2-bromopyridine-6-methanol (*Tetrahedron Lett.*, 1996, 50, 2537) following the procedure given for Reference Example 1. The product was isolated by addition of water to the reaction mixture and the resulting precipitate was filtered off. Flash chromatography on silica gel, eluting with ethyl acetate, and recrystallisation (ethyl acetate-methanol) gave the title-phthalazine, mp 247.5–249° C.; $^1$H NMR (360 MHz, CDCl$_3$) δ2.61 (3H, d J=0.7 Hz, Me), 5.73 (2H, s, CH$_2$), 6.82 (1H, d, J=0.7 Hz, Ar—H), 7.48 (1H, d, J=7.8 Hz, Ar—H), 7.63 (1H, t, J=7.7 Hz, Ar—H), 7.76 (1H, d, J=7.4 Hz, Ar—H) 7.84 (1H, t, J=8.4 Hz, Ar—H), 7.98 (1H, t, J=8.4 Hz, Ar—H), 8.31 (1H, d, J=8.5 Hz, Ar—H), 8.70 (1H, d, Ar—H); MS (ES$^+$) m/e 437 [MH]$^+$; Anal. Found C, 52.27; H, 2.85; N, 19.14. C$_{19}$H$_{13}$N$_6$O$_2$ Br. 0.1 (H$_2$O) requires C, 51.98; H, 3.03; N, 18.60%.

INTERMEDIATE 2

6-Hydroxy-3-(5-Methylisoxazol-3-yl)-1,2,4-triazolo[3,4-a]phthalazine

A solution of sodium hydroxide (0.67 g, 17 mmol) in water (7.5 ml) was added to a stirred solution of Intermediate 1 (1.0 g, 3.5 mmol) in dioxane (37.5 ml) and the mixture heated at reflux for 4 h. The solvent was evaporated in vacuo and the residue partitioned between water and diethyl ether. The aqueous layer was separated, washed with ether (×1) and then acidified with 2N hydrochloric acid until pH2 was attained. The solid which precipitated out of solution was filtered off and the aqueous filtrate extracted with dichloromethane (×3). The combined extracts were dried (MgSO$_4$) and evaporated in vacuo and combined with the precipitate to give the title-product (0.45 g, 48%), $^1$H NMR (250 MHz, d$^6$-DMSO) δ2.58 (3H, d, J=0.7 Hz, Me), 7.07 (1H, d, J=0.9 Hz, Ar—H), 7.94 (1H, m, Ar—H), 8.08 (1H, m, Ar—H), 8.24 (1H, d, J=7.4 Hz, Ar—H), 8.54 (1H, d, J=7.4 Hz, Ar—H), 13.32 (1H, br s, NH); MS (ES$^+$) m/e 268 [MH]$^+$.

Reference Example 3

3-(5-Methylisoxazol-3-yl)-6-(1H-1,2,3-triazol-5-yl)methyloxy-1,2,4-triazolo[3,4-a]phthalazine a) 5-Formyl-1-[2-(trimethylsilyl)ethoxy]methyl-1,2,3-triazole n-Butyl lithium (6.8 ml of a 1.6M solution in hexanes, 10.9 mmol) was added dropwise over 0.08 h to a stirred solution of 1-[2-(trimethylsilyl)ethoxy]methyl-1,2,3-triazole (J. Heterocycl. Chem., 1992, 29, 1203) (2.077 g, 10.42 mmol) in THF (30 ml) at −78° C. under nitrogen. The solution was allowed to warm to −60° C. over 0.67 h, then recooled to −78° C. and DMF (0.9 ml, 11.6 mmol) added. The mixture was allowed to warm to room temperature and stirred for 16.5 h. Saturated ammonium chloride solution (50 ml) was added and the reaction mixture extracted with diethyl ether (3×80 ml). The combined ethereal extrants were dried (MgSO$_4$), evaporated in vacuo, and the residue chromatographed on silica gel, eluting with 30% ethyl acetate/hexane, to give the title-triazole (1.713 g, 72%), $^1$H NMR (360 MH$_2$, CDCl$_3$) δ0.01 (9H, s, Me$_3$Si), 0.92–0.99 (2H, m, CH$_2$), 3.64–3.69 (2H, m, CH$_2$), 6.05 (2H, s, CH$_2$), 8.31 (1H, s, Ar—H), 10.12 (1H, s, CHO).

b) 5-Hydroxymethyl-1-[2-(trimethylsilyl)ethoxy]methyl-1,2,3-triazole

Sodium borohydride (0.284 g, 7.51 mmol) was added to a stirred solution of the preceding triazole (1.704 g, 7.495 mmol) in methanol (8 ml) at 0° C. under nitrogen. The mixture was stirred at 0° C. for 0.5 h and at room temperature for 0.5 h. Water was added and the mixture partitioned between dichloromethane and saturated brine. The aqueous layer was separated and further extracted with dichloromethane (×2). The combined organic layers were dried ((MgSO$_4$) and evaporated in vacuo and the residue chromatographed on silica gel, eluting with 70% ethyl acetate/hexane, to give the title-product (1.34 g, 78%), $^1$H NMR (360 MHz, CDCl$_3$) δ0.00 (9H, s, Me$_3$Si), 0.90–0.95 (2H, m, CH$_2$), 3.58–3.63 (2H, m, CH$_2$), 4.84 (2H, s, CH$_2$), 5.80 (2H, s, CH$_2$), 7.68 (1H, s, Ar—H).

c) 3-(5-Methylisoxazol-3-yl)-6-{1-[2-(trimethylsilyl)ethoxy]methyl-1,2,3-triazol-5-yl}methyloxy-1,2,4-triazolo[3,4-a]phthalazine The title-compound was prepared from Intermediate 1 and the preceding alcohol following the procedure described for Example 10, 360 MHz (360 MHz, CDCl$_3$s) δ0.00 (9H, s, Me$_3$Si), 0.88–0.93 (2H, m, CH$_2$), 2.63 (3H, s, Me), 3.61–3.66 (2H, m, CH$_2$), 5.92 (2H, s, CH$_2$), 5.97 (2H, s, CH$_2$), 6.89 (1H, s, Ar—H), 7.86 (1H, m, Ar—H), 8.02 (1H, t, J=7.7 Hz, Ar—H), 8.18 (1H, s, Ar—H), 8.23 (1H, d, J=8.0 Hz, Ar—H), 8.76 (1H, d, J=8.0 Hz, Ar—H); MS (ES$^+$) m/e 479 [MH]$^+$.

d) 3-(5-Methylisoxazol-3-yl)-6-(1H-1,2,3-triazol-5-yl)methyloxy-1,2,4-triazolo[3,4-a]phthalazine A mixture of the preceding product, ethanol (10 ml) and 2N HCl (20 ml) was heated at 50° C. for 15.25 h. The solution was basified to pH 12 with saturated sodium carbonate solution and the solvents evaporated in vacuo. The residue was azeotroped with ethanol (×2) and chromatographed on silica gel, eluting with 0–4% methanol/dichloromethane (gradient elution), to give the title-product, $^1$H NMR (400 MHz, CDCl$_3$) δ2.65 (3H, s, Me), 5.73 (2H, s, CH$_2$), 7.02 (1H, s, Ar—H), 7.87 (1H, t, J=7.8 Hz, Ar—H , 7.99–8.03 (2H, m, 2 of Ar—H), 8.24 (1H, d, J=8.2 Hz, Ar—H) 8.72 (1H, d, J=7.9 Hz, Ar—H); MS (ES$^+$) m/e 349 [MH]$^+$.

EXAMPLE 1

3-(5-Methylisoxazol-3-yl)-6-(1-methyl-1,2,3-triazol-5-yl)methyloxy-1,2,4-triazolo[3,4-a]phthalazine, 3-(5-methylisoxazol-3-yl)-6-(2-methyl-1,2,3-triazol-4-yl)methyloxy-1,2,4-triazolo[3,4-a]phthalazine and 3-(5-methylisoxazol-3-yl)-6-(1-methyl-1,2,3-triazol-4-yl)methyloxy-1,2,4-triazolo[3,4-a]phthalazine Lithium hexamethyldisilazide (1.63 ml of a 1M solution in THF, 1.63 mmol) was added dropwise to a stirred solution of 3-(5-methylisoxazol-3-yl)-6-(1H-1,2,3-triazol-5-yl)methyloxy-1,2,4-triazolo[3,4-a]phthalazine (241 mg, 0.626 mmol) prepared as in Reference Example 3 in DMF (50 ml) at −31° C. under nitrogen. The mixture was warmed to −23° C. over 1.5 h, methyl iodide (0.10 ml, 1.6 mmol) added dropwise and the reaction mixture allowed to warm to room temperature overnight. Water was added and the solvent evaporated in vacuo. The residue was partitioned between dichloromethane and water and the aqueous phase separated and re-extracted with dichloromethane (×1). The combined organic extrants were washed with brine (×1), dried (MgSO$_4$) and evaporated in vacuo. Chromatography of the residue on silica gel, eluting with 0–5% methanol/dichloromethane (gradient elution), followed by preparative HPLC (YMC Sil column, 250×20 mm) eluting with 5% methanol/1-chlorobutane, separated the triazole isomers:

Least polar isomer (HPLC solvent system): 3-(5-methylisoxazol-3-yl)-6-(2-methyl-1,2,3-triazol-4-yl)methyloxy-1,2,4-triazol[3,4-a]phthalazine $^1$H NMR (400 MHz, CDCl$_3$) δ2.59 (3H, s, Me), 4.21 (3H, s, Me), 5.73 (2H, s, CH$_2$), 6.89 (1H, s, Ar—H), 7.79 (1H, m, Ar—H), 7.94 (1H, m, Ar—H), 8.10 (1H, s, Ar—H), 8.22 (1H, d, J=8.0 Hz, Ar—H), 8.67 (1H, d, J=8.0 Hz, Ar—H); MS (ES$^+$) m/e 363 [MH]$^+$.

Intermediate polarity isomer: 3-(5-methylisoxazol-3-yl)-6-(1-methyl-1,2,3-triazol-4-yl)methyloxy-1,2,4-triazolo[3,4-a]phthalazine $^1$NMR (400 MHz, CDCl$_3$) δ2.60 (3H, s, Me), 4.09 (3H, s, Me), 5.78 (2H, s, CH$_2$), 6.90 (1H, d, J=0.8 Hz, Ar—H), 7.80 (1H, m, Ar—H), 7.94 (1H, m, Ar—H), 8.25 (1H, d, J=8.0 Hz, Ar—H), 8.65 (1H, d, J=8.0 Hz, Ar—H), 8.73 (1H, s, Ar—H); MS (ES$^+$) m/e 363 [MH]$^+$.

Most polar isomer (HPLC solvent system): 3-(5-methylisoxazol-3-yl)-6-(1-methyl-1,2,3-triazol-5-yl)methyloxy-1,2,4-triazolo[3,4-a]phthalazine $^1$H NMR (400 MHz, CDCl$_3$) δ2.56 (3H, s, Me), 4.19 (3H, s, Me), 5.76 (2H, s, CH$_2$), 6.82 (1H, s, Ar—H), 7.80 ($^1$H, m, Ar—H), 7.96 (1H, m, Ar—H), 804 (1H, s, Ar—H), 8.12 (1H, d, J=8.8 Hz, Ar—H), 8.67 (1H, d, J=8.0 Hz, Ar—H); MS (ES$^+$) m/e 363 [MH]$^+$.

What is claimed is:

1. A method of enhancing cognition in a subject suffering from Alzheimer's disease which comprises administering to that subject a cognition enhancing amount of 3-(5-Methylisoxazol-3-yl)-6-(1-methyl-1,2,3-triazol-4-yl)methyloxy-1,2,4-triazolo[3,4-a]phthalazine.

2. A method of enhancing cognition in a subject suffering from Alzheimer's disease which comprises administering to that subject a cognition enhancing amount of a pharmaceutical composition comprising 3-(5-Methylisoxazol-3-yl)-6-(1-methyl-1,2,3-triazol-4-yl)methyloxy-1,2,4-triazolo[3,4-a]phthalazine and a pharmaceutically acceptable carrier.

* * * * *